United States Patent [19]

Fountoulakis et al.

[11] Patent Number: 5,137,813
[45] Date of Patent: Aug. 11, 1992

[54] **PROCESS FOR PRODUCTION OF AN ANTIBIOTIC COMPOUND USING *ZALERION ARBORICOLA***

[75] Inventors: Jimmy M. Fountoulakis, Westfield; Prakash S. Masurekar, Warren, both of N.J.

[73] Assignee: Merck & Co., Inc., Rahway, N.J.

[21] Appl. No.: 539,945

[22] Filed: Jun. 18, 1990

[51] Int. Cl.$^5$ .................. C12P 21/04; C12N 1/14; C12N 1/00
[52] U.S. Cl. .................. 435/71.3; 435/71.1; 435/71.2; 435/171; 435/254; 435/911
[58] Field of Search .................. 435/71.1–71.3, 435/71, 254, 911

[56] References Cited

U.S. PATENT DOCUMENTS 4,931,352  6/1990  Fromtling et al. .
4,968,608  11/1990  Giacobbe et al. .................. 435/71

FOREIGN PATENT DOCUMENTS 2065130A  6/1981  United Kingdom .

OTHER PUBLICATIONS

D. A. Hopwood, "Isolation of Mutants", Ch. VI, pp. 363–433, Methods in Microbiology, vol. 3A, Academic Press, 1970.
C. T. Calam, "Improvement of Microorganisms by Mutation, Hybridization & Selection" Ch. VII, pp. 435–459, Methods in Microbiology, vol. 3A, Academic Press, 1970.
R. E. Schwartz et al., J. Antibiotics 42, 163–167 (1989).
C. F. Wichmann et al., J. Antibiotics 42, 168,173 (1989).

*Primary Examiner*—Douglas W. Robinson
*Assistant Examiner*—L. Blaine Lankford
*Attorney, Agent, or Firm*—Alice O. Robertson; Hesna J. Pfeiffer

[57] ABSTRACT

A process for producing an antibiotic compound which is normally one of several minor components in the cultivation of *Z. arboricola* ATCC 20868 to be the primary product is described.

2 Claims, No Drawings

PROCESS FOR PRODUCTION OF AN ANTIBIOTIC COMPOUND USING *ZALERION ARBORICOLA*

BACKGROUND OF THE INVENTION

1-[N$^2$-(10,12-dimethyl-1-oxo-tetradecyl) ornithine]-4-[4-(4-hydroxyphenyl)-2-aminobutanoic acid]-5-(3-hydroxyglutamine)echinocandin B having the formula

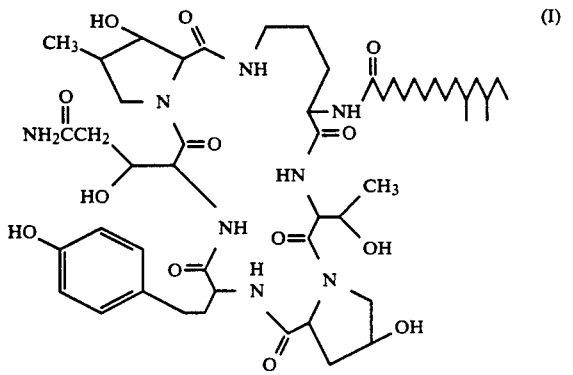

(I)

(hereinafter Compound I) and useful as an antibiotic agent as described and claimed in copending application Ser. No. 374,418, filed Jun. 30, 1989 and in copending application Ser. No. 492,025, filed Mar. 12, 1990 is normally produced as one of the minor components on the cultivation of MF 5171 *Zalerion arboricola* ATCC 20868.

Compound I is a white solid having the following spectral characteristics:

MASS SPECTRAL DATA

Electron impact (EI) mass spectral data were obtained on a Finnigan-MAT 212 mass spectrometer at 90 eV. Gas Chromatograph-Mass Spectrogram (GC-MS) analyses of the TMS (trimethylsilyl) derivatives of total acid hydrolysates were performed on the same instrument. Fast atom bombardment (FAB) mass spectra were recorded on a VG20-253 or Finnegan MAT 90 instrument.

Compound I has a molecular weight 1014 by FAB-MS (observed (M+Na)$^+$ at m/z 1037). GC-MS of the total acid hydrolysate disclosed one equivalent each of threonine, 4-hydroxyproline, 3-hydroxy-4-methylproline, 3-hydroxyglutamic acid, and a C16:0 saturated fatty acid. The HR-FAB-MS from [M+Cs]$^+$ ion indicates the molecular formula to be $C_{51}H_{82}N_8O_{13}$ (Calcd. 1014.6001, Found 1014.5915.)

NMR SPECTRAL DATA $^1$H and $^{13}$C NMR spectra were recorded in CD$_3$OD at ambient temperature on Varian XL300 and XL400 spectrometers. Chemical shifts are indicated in upper relative to TMS at zero ppm using the solvent peak at δ3.30 and 49.0 ppm as internal standards for $^1$H and $^{13}$C NMR spectra respectively.

Compound I $^1$H NMR Spectrum in CD$_3$OD at 400 MHz is seen in FIG. 1.

$^{13}$C NMR Chemical Shifts: obtained in CD$_3$OD at 100 MHz.

11.2, 11.6, 19.8, 20.2, 20.7, 24.6, 27.0, 28.0(2×), 30.27, 30.33, 30.5, 30.7, 31.1, 31.2, 32.9(2×), 33.9, 36.7, 38.0, 38.3, 38.5, 39.0, 40.1, 45.9, 52.8, 53.0, 55.2, 55.7, 57.1, 58.6, 62.1, 68.2, 70.3, 70.7, 71.3, 76.0, 116.3(2×), 130.5(2×), 133.0, 156.7, 170.2, 172.2, 172.7, 173.60, 173.63, 175.2, 176.3, 176.5 ppm.

It has however not been possible to produce it in a significant amount or in an amount to exceed Compound X of the following structure:

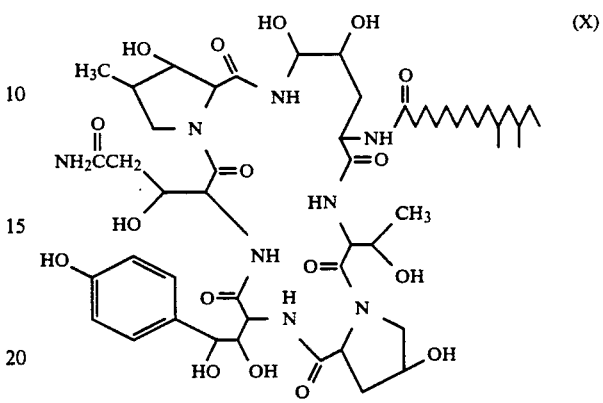

(X)

(Compound X is the major metabolite of naturally occurring *Zalerion arboricola*, ATCC 20868. It is described and claimed in application Ser. No. 362,647, filed Jun. 7, 1989 now U.S. Pat. No. 4,931,352, Jun. 5, 1990 which is a continuation of Ser. No. 105,795 filed Oct. 7, 1987, now abandoned.)

DESCRIPTION OF THE INVENTION

According to the present invention there has been discovered a method whereby Compound I may be produced as the primary product with substantial complete absence of Compound X.

The method of the present invention for producing Compound I as the primary product comprises cultivating a particular mutant of *Zalerion arboricola* identified as ATCC 20988 under aerobic conditions in a suitable medium containing assimilable sources of carbon, nitrogen and inorganic salts until a substantial amount of antifungal activity is produced as determined by assay against *Candida albicans* or by comparing with a previously prepared HPLC retention spectra as standard.

The mutant of *Z. arboricola* suitable for this process of the present invention is that maintained in the Merck Culture Collection as MF 5416 which was produced by mutagenic treatment of *Z. arboricola* MF5405, ATCC 20958, which in turn was produced by mutagenic treatment of naturally occurring *Z. arboricola* maintained in the Merck Culture Collection as MF5171, and deposited at the American Type Culture Collection as ATCC 20868. MF 5416 has been deposited in the permanent culture collection of the American Type Culture Collection, 2301 Parklawn Drive, Rockville, Md. 20852 and is accessible under the accession number ATCC 20988.

The colonial and morphological description of ATCC 20988 are as follows:

Colonies on potato-dextrose agar (Difco) at 20° C. slow-growing, attaining a diameter of 8–12 mm in one week. Mature colonies (3–4 weeks) on potato-dextrose agar effuse, with submerged and aerial hyphae, surface hairy, lanose, or funiculose, dull to moderately shiny, forming raised, densely compact colonies, with a substromatic texture due to dense conidia formation. Colony color pale olive-brown, olive, olive-brown, finally olive-black, Isabella Color, Sayal Brown, Tawny-olive, Saccardo's Umber, Sepia, Brownish Olive, Raw Umber, Dark Olive, Olivaceous Black (capitalized color names from R. Ridgway. 1912. Color Standards and Nomenclature, Washington, D.C.). Same colors in colony reverse. Odor, exudates, and soluble pigments absent.

Hyphae (in 3% KOH) pale yellow-brown to olive-brown, septate, branched, often with irregular lateral or terminal lobes, 1–3 μm wide, thin- to slightly thick-walled, with walls smooth to slightly incrusted or verrucose. Aerial hyphae often adhering together in fascicles. Setae and hyphopodia absent.

Conidiogenous cells monoblastic, scattered to dense, integrated, terminal and intercalary, arising directly from undifferentiated hyphae, at right to slightly acute angles. Conidia originating as irregular chains, filaments, or coils, later developing as compact, irregular masses of 6–25 cells. Individual conidial cells, 3–6 μm in diameter, globose, subglobose, or slightly irregular to lobed, smooth to finely verruculose, yellow-brown to olive brown.

For the production of the mutant, any of the agents commonly used to produce mutants may be employed. Thus, ultraviolet radiation, chemical mutagens, or intercalating agent may be employed. Suitable chemical mutagens include N-nitroso-N-methylurethane and N-methyl-N'-nitro-N-nitrosoguanidine. The latter is preferred.

The mutant may be produced by growing a culture of the parent microorganism Z. arboricola ATCC 20958 on potato dextrose agar at 25° C. for three weeks, then adding 0.3M TRIS buffer of pH 7 to the agar surface and mechanically transferring the spores into the buffer. The spore suspensions are decanted, the procedure repeated, and the suspensions combined and filtered to remove large clusters. The suspension filtrate is centrifuged first at 600 rpm, then at 700 and 800 rpm retaining the supernatant liquid each time, thereby removing large clusters of spores, then centrifuging at 3000 rpm and retaining the pellet. The pellet is resuspended in 0.3M TRIS buffer at pH7 and subjected to mutation.

The mutation may be carried out by treating the spore suspension in 0.3M TRIS buffer at pH 7 to a mutagen such as N-methyl-N'-nitro-N-nitrosoguanidine at ambient temperature while shaking. The mutagen is removed by centrifugation, the pellet is washed with 0.3 TRIS buffer, then resuspended in the buffer and thereafter plated on potato dextrose agar and incubated at 25° C. for two weeks to obtain growth of colonies. The colonies are isolated and are transferred to slants of the same medium for use and for retention. One of the colonies thus obtained is Z. aboricola which was tentatively identified as Z13-62 and subsequently maintained as MF 5416 and deposited as ATCC 20988.

The process of the present invention is carried out by cultivating Z. arboricola ATCC 20988 in a nutrient medium containing assimilable sources of carbon, nitrogen and inorganic salts until a substantial amount of Compound I has been produced.

Suitable sources of carbon include sugars, sugar alcohols such as mannitol, glycerol, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 15 percent by weight of the medium is satisfactory. One or several carbon sources may be employed in the same medium.

The sources of nitrogen include amino acids such as glycine, arginine, threonine, methionine and the like, ammonium salts, as well as complex sources such as yeast hydrolysates, yeast autolysates, yeast extracts, corn steep liquors, distillers solubles, cottonseed meal, meat extract, casein hydrolysates and the like. The various sources of nitrogen can be used alone or in combination in amounts ranging from 0.2 to 10 percent by weight of the medium.

Among the nutrient salts, which can be incorporated in the culture media are the customary inorganic salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

In producing the compounds, the culture is first grown in a seed medium and thereafter the culture is cultivated in a medium for production of the desired metabolite. A typical seed medium has the following composition:

| KF Seed Medium | per liter |
| --- | --- |
| Cerelose | 10 g |
| Corn steep liquor | 5 g |
| Tomato paste | 40 g |
| Oat flour | 10 g |
| Trace elements | 10 ml |

The trace element mixture is of the following composition:

| | Per liter of 0.6N HCl |
| --- | --- |
| $FeSO_4.7H_2O$ | 1.0 g |
| $MnSO_4.4H_2O$ | 1.0 g |
| $CuCl_2.2H_2O$ | 0.025 g |
| $CaCl_2$ | 0.1 g |
| $H_3BO_3$ | 0.056 g |
| $(NH_4)_6Mo_7O_{24}.4H_2O$ | 0.01 g |
| $ZnSO_4.7H_2O$ | 0.2 g |

Although conventional nutrient production media may be employed, media containing certain nutrients such as mannitol and hydrolyzed casein or milk protein favors the production of the desired compound, and especially useful are the production media listed below which have previously been described in copending application Ser. No. 374,416, filed Jun. 30, 1989, in a copending continuation-in-part application Ser. No. 492,025, filed Mar. 12, 1990, and copending application Ser. No. 492,025, filed Mar. 12, 1990.

One of the media that is preferred is Medium I of the following composition:

| Medium I (S6) | Per liter |
| --- | --- |
| D Mannitol | 44 g |
| $KH_2PO_4$ | 2 g |
| Glycine | 2 g |
| Peptonized Milk | 15 g |
| Lactic acid | 2 g |
| Trace elements | 10 ml |
| Soybean oil | 10 g | pre-sterilization pH 7.0

Another especially useful medium is Medium II and is of the following composition:

| Medium II (TG 103) | Per liter |
| --- | --- |
| D-Mannitol | 40 g |
| NZ-Amine (type E)* | 33 g |
| Fidco-Yeast Extract | 10 g |
| (NH$_4$)$_2$SO$_4$ | 5 g |
| KH$_2$PO$_4$ | 9 g | no pH adjustment
*Casein hydrolysate, Humko-Sheffield, Memphis, Tenn.

Still another useful medium is Medium III of the following composition:

| Medium III (TG 102) | Per liter |
| --- | --- |
| D-Mannitol | 40 g |
| Bacto-Peptone | 33 g |
| Bacto-Yeast Extract | 10 g |
| (NH$_4$)$_2$SO$_4$ | 5 g |
| KH$_2$PO$_4$ | 9 g | no pH adjustment

The fermentation production medium inoculated with the culture growth is incubated for 3 to 30 days, usually 7 to 14 days, with or without agitation. The fermentation may be conducted aerobically at temperatures ranging from about 20° C. to about 40° C. For optimum results, it is most convenient to conduct these fermentations at a temperature in the range of from about 24° C. to about 30° C. Temperatures of about 24°-28° C. are most preferred. The pH of the nutrient medium suitable for producing the instant compounds can vary from about 5.0 to 8.5 with a preferred range of from about 5.5 to 7.5. After the appropriate period for the production of Compound I as determined by bioassay or HPLC against a previously established retention spectrum, Compound I may be harvested.

Compound I may be harvested from the fermentation medium by adding a water-immiscible organic solvent to the fermentation broth, separating and recovering the organic solution, vaporizing off the solvent to obtain Compound I as residue.

Alternatively, methanol may be added to the fermentation medium and after thorough mixing, filtered. The methanol solution may be evaporated to dryness to recover crude product residue, and the residue then dissolved in methanol for HPLC analysis and purification using silica gel chromatography with ester/alcohol mixtures with increasing concentration of alcohol for elution or preferably HPLC with C$_{18}$ reverse phase resin.

Isolation procedures for Compound I described in the aforementioned copending application, Ser. No. 374,418, also may be employed. However, with the elimination of a number of minor products in the process according to the present invention, the isolation procedure which employs chromatographic procedures is greatly simplified and the number of chromatographic separations necessary is greatly reduced.

The process of the present invention, Compound I may be prepared substantially without the co-production of Compound X. Compound Y having the structure below is the only other significant product and thus, may be separated without great difficulty. Thus, a facile method for the production of Compound I is provided.

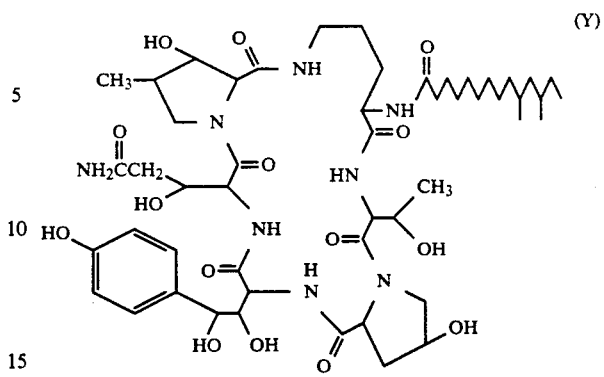

(Y)

Compound I has superior properties against fungal organisms giving rise to mycotic infections such as *Candida albicans, Candida tropicalis* and *Candida parapsilosis*, as well as against parasitic organisms such as *Pneumocystis carinii*. Thus, for example, fungicidal effectiveness in the range of from 0.5 to 4.0 μg/ml against six strains of *Candida albicans* can be demonstrated in a microbroth dilution assay employing Yeast Nitrogen Base (Difco) with 1 percent dextrose as the medium as more fully described in the aforecited copending application. Also mice with induced *P. carinii* infections when treated by twice daily injection of aqueous medium containing at a dose of 2.0 μg/kg of Compound I in DMSO for seven weeks and then sacrfified and the lung tissue processed and compared with that of mice treated with aqueous DMOS vehicle control were found to have less cysts than the controls. For such therapeutic use Compound I may be administered in a therapeutically effective or anti-infective amount to subjects infected with or to immune compromised subjects susceptible of being infected with Candida species or with *Pneumocystis carinii* as more fully disclosed in the aforecited copending application.

The following examples illustrate the invention but are not to be construed as limiting.

EXAMPLE I

A. Preparation of Mutant *Z. arboricola* ATCC 20988

A culture of *Z. arboricola* ATCC 20958 was grown on potato dextrose agar in petri plates at 25° C. for 3 weeks. Ten milliliters of 0.3M TRIS buffer, pH 7, were added to the plates and the spores scraped off the surface into the buffer with a sterile cotton swab. The suspension in the buffer was decanted off and the procedure repeated twice. The spore suspensions were combined and filtered through glass wool to remove large clusters of spores. The suspension filtrate was centrifuged first at 600 rpm for 3 minutes, the pellet discarded and the supernatant then centrifuged at 700 rpm for three minutes and the procedure repeated with the final centrifugation being at 800 rpm. The supernatant liquid from the third centrifugation was then centrifuged at 3000 rpm for 5 minutes. The pellet from this centrifugation was resuspended in 3 milliliters of 0.3M TRIS buffer at pH 7 and used for mutagenic treatment. This suspension contained from 10$^3$ to 10$^4$ spores per milliliter.

To the spore suspension was added 1 mg/ml of N-nitroso-N-methylguanidine and the resulting mixture shaken at 300 rpm for 30 minutes at room temperature. At the end of this period, the mixture was centrifuged and the supernatant liquid was removed. The pellet was washed twice with 0.3M TRIS buffer pH 7.0 and then resuspended in the same buffer and after appropriate dilutions plated on potato dextrose agar for forming isolated colonies. The plates were incubated at 25° C. for two weeks for colony formation. The colonies were isolated by separately transferring to slants of potato dextrose agar. The inoculated slants were incubated at 25° C. for 10–14 days and a plug of mycelial growth from the slants taken and tested for the production of Compounds I and X, and other components in the fermentation by HPLC assay. A plug from one of the slants initially designated as Z13-62, which subsequently was placed in the Merck Culture Collection as MF 5416 and deposited with the American Type Culture Collection as ATCC 20988, was employed in the following fermentation.

B. Production of Compound I Fermentation and Harvest

Seed cultures were first prepared by inoculating twenty milliliters of KF seed medium (previously defined) in an unbaffled Erlenmeyer flask with a plug from the slant identified as Z13-62. The flasks were shaken at 220 rpm and 25° C. for 96 hours to produce a seed culture.

Forty milliliters of Medium I (S6) in 250 milliliters of unbaffled Erlenmeyer flask was inoculated with 2 milliliters of the seed developed as described above. The inoculated flasks were shaken at 220 rpm and 25° C. for 14 days and the contents then analyzed for the production of the secondary metabolites by HPLC assay.

After completion of the cultivation the broth was homogenized and to twenty milliliters of the broth was added an equal volume of methyl ethyl ketone and the mixture shaken for 30 minutes on a reciprocating shaker. The organic and aqueous phases were separated by centrifugation at 3000 rpm and the methyl ethyl ketone layer evaporated to dryness in vacuo to obtain a residue. The latter was dissolved in 1 milliliter of methanol and centrifuged for 5 minutes. The resulting clarified solution was diluted with methanol and recentrifuged. The supernatant was then subjected to an HPLC analysis carried out using the following conditions:

Column: Whatman Partisil C18 ODS-3,5 μm, 25 cm
Solvent: Water/Acetonitrile, 54/46
Flow rate: 0.75 ml/min
Column temperature: 40° C.
Detection: 210 nm The fractions were collected with a commercial fraction collector, fitted with 96 well, flat bottom, microtiter plates at a rate of one fraction per 0.3 minute. After completion of the collection, the HPLC solvent was evaporated in a high speed vacuum concentrator. Then to each well was added 0.2 milliliter of potato dextrose broth which previously had been inoculated with *Candida albicans* MY 1028 and grown for 24 hours. The volume of the inoculum was 0.2 milliliter per 100 milliliters of medium. The plates were then incubated at 37° C. overnight and observed for growth. The fractions which were bioactive inhibited the growth of *C. albicans* MY 1028.

The bioactivity results showed the primary product to be that with a relative retention time of 2.7 which was subsequently identified as Compound I. The amount of Compound I produced was 64 μg/ml. Compound X and two unidentified components were produced in insignificant amounts. The amount of Compound X produced was 3 μg/ml. Compound Y was produced as a significant by-product of 53 μg/ml.

Similarly, seed cultures were prepared from the parent by inoculating a plug from MF 5405 into KF seed medium and the inoculated medium shaken at 220 rpm and 25° C. for 96 hours. Forty milliliters of Medium I (S6) in 250 milliliters of unbaffled Erlenmeyer flask was inoculated with 2 milliliters of the seed culture. The inoculated flasks were shaken at 220 rpm and 25° C. for 14 days and the contents analyzed for the production of the secondary metabolites by the HPLC assay. The broth then was extracted with methyl ethyl ketone and the organic layer evaporated to dryness to recover the metabolite as residue. The residue was dissolved in methanol and subjected to HPLC as above described and the fractions collected in the microtiter plate fraction collector. The wells then were filled with potato dextrose broth which previously had been inoculated with *C. albicans* MY 1028, and the plate incubated and observed for growth.

The bioactive fractions were correlated with relative retention time determined for the various components produced during cultivation of *Z. arboricola* MF 5405 (ATCC 20958). The results of the amounts of compounds produced as determined from HPLC chromatogram and compared with a previously prepared reference standard were as follows:

| Culture | Compound I | Compound X | Compound Y |
|---|---|---|---|
| | | μg/l | |
| MF 5405 (parent) | — | — | 345 |
| MF 5416 (mutant) | 64 | 3 | 53 |

EXAMPLE II

A plug from a culture of *Z. arboricola* MF Z13-62 on slants of potato dextrose agar medium (Difco) was inoculated into 20 milliliters of KF-medium in a 250 milliliter unbaffled Erlenmeyer flask and the flask shaken at 220 rpm and 25° C. for five days.

Two milliliters of the culture bearing seed medium were used to inoculate each of forty 250 milliliters unbaffled Erlenmeyer flasks containing 40 milliliters of S6 medium and the media grown by shaking at 220 rpm at 25° C. for 14 days. The contents of the flasks were pooled to obtain a volume of about 1.5 liters. A twenty milliliter sample was taken for HPLC analysis and bioactivity and found to have produced 130 μg/ml of a compound having relative retention time of 2.7.

The remainder was employed for isolation. 1500 milliliters of methanol was added and the mixture stirred for several hours and then filtered. The spent cells were extracted twice with 2 liters of methanol and the extracts were combined to obtain 4200 milliliters. It was diluted with an equal volume of water and absorbed to 400 milliliters of SP-207 "Diaion" (Mitsubishi Chemical Industries, Ltd.) column (pre-equilibrated with MeOH/H$_2$O 1:1) at 40 ml/min. The column was washed with 400 milliliters of MeOH/H$_2$O 1:1 and eluted with 100 percent methanol. Two hundred milliliter eluates were monitored by analytical HPLC. Fractions 2–12 were combined to obtain 2 liters of product rich material. This was diluted with 2 liters of water and absorbed to 400 milliliters of "Diaion" HP-20 column (pre-equilibrated with methanol/water (1:1)). The column was then washed with 800 milliliters of 65% methanol and eluted with 100 percent methanol. Five fractions of 200 milliliters each were combined and concentrated to dryness to obtain 500 milligrams of residue.

Ninety-eight milligrams of this residue was intimately admixed with 4 milliliters of 84 percent methanol in water and chromatographed (DuPont "Zorbax" ODS 21.2 mn×25 cm 8 μm semi-preparative HPLC column). The initial solvent system was methanol/water (68/32) at 20 ml/min and the effluent monitored via UV at 210 nm and analytical HPLC of the fractions. The mobile phase composition was adjusted twice first to methanol/water (70/30) and then to methanol/water (75/25). Fraction 65-67 were combined and concentrated to obtain 12.1 mg of a compound identified as Compound I. The only other compound produced in significant amount was Compound Y. Compound X was not produced in any significant amount.

What is claimed is:

1. A method for producing a compound having the formula:

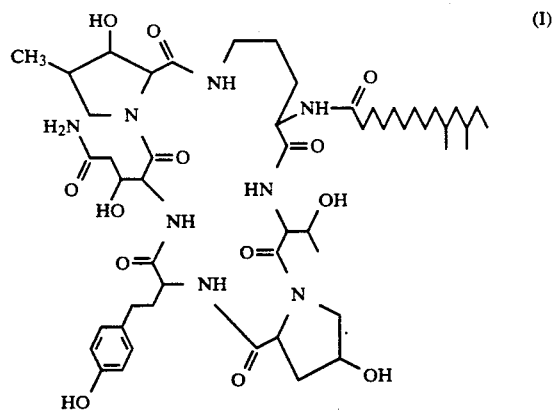

as the primary product comprising cultivating MF 5416 *Zalerion arboricola* ATCC 20988 in a nutrient medium containing assimilable sources of carbon, nitrogen and inorganic salts under aerobic conditions until production of the compound of formula (I) is substantially complete and thereafter separating the product from the medium.

2. A biologically pure culture of *Zalerion arboricola* ATCC 20988.

* * * * *